United States Patent [19]

Kreinick et al.

[11] Patent Number: 4,834,104
[45] Date of Patent: May 30, 1989

[54] METHOD AND APPARATUS FOR MEASURING SPECIFIC GRAVITY OF A FLOWING LIQUID

[75] Inventors: Stephen J. Kreinick; Larry K. Blankenship, both of San Diego, Calif.

[73] Assignee: C. R. Bard, Inc., Murray Hill, N.J.

[21] Appl. No.: 762,146

[22] Filed: Aug. 1, 1985

[51] Int. Cl.$^4$ .............................................. A61B 5/00
[52] U.S. Cl. .................................... 128/633; 128/771; 73/32 R; 356/136
[58] Field of Search ............... 128/632, 633, 771, 664, 128/665; 356/134–137; 73/32 R

[56] References Cited

U.S. PATENT DOCUMENTS

| | | | |
|---|---|---|---|
| 2,780,131 | 2/1951 | Lanneau et al. | 356/136 |
| 3,487,069 | 12/1969 | Maselli | 356/135 |
| 3,628,867 | 12/1971 | Brady | 356/136 |
| 3,650,631 | 3/1972 | Grassel et al. | 356/136 |
| 3,770,352 | 11/1973 | White | 356/136 |
| 3,923,401 | 12/1975 | Llop et al. | 356/135 |
| 4,381,895 | 5/1983 | Hughes et al. | 356/134 |
| 4,446,871 | 5/1984 | Imura | 128/633 |
| 4,448,207 | 5/1984 | Parrish | 128/771 |
| 4,504,263 | 3/1985 | Stener et al. | 128/DIG. 13 |
| 4,571,075 | 2/1986 | Kamrat | 356/136 |
| 4,664,124 | 5/1987 | Ingle et al. | 128/771 |

FOREIGN PATENT DOCUMENTS 0152438 11/1980 Japan .................................. 356/136

Primary Examiner—Kyle L. Howell
Assistant Examiner—John C. Hanley
Attorney, Agent, or Firm—Freilich, Hornbaker, Rosen & Fernandez

[57] ABSTRACT

A method and apparatus for continually measuring the specific gravity of a flow liquid. The liquid is caused to flow across a flat measurement surface defined by a light transmissive shelf member. The measurement surface, i.e. the interface between the shelf member and liquid sample thereon, is illuminated by rays incident at angles greater than and less than a critical angle to reflect a boundary line whose position is dependent on the critical angle and thus the specific gravity of the liquid sample. The reflected boundary line is projected onto a photovoltaic surface which, together with detector electronics, determines the position of the boundary line with respect to a boundary line position associated with a reference liquid. The difference in boundary line position is used by the detector electronics to determine the specific gravity of the sample by a table lookup procedure.

7 Claims, 6 Drawing Sheets

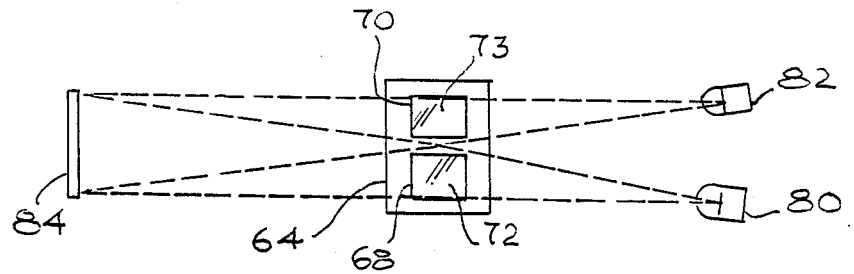
Fig. 6
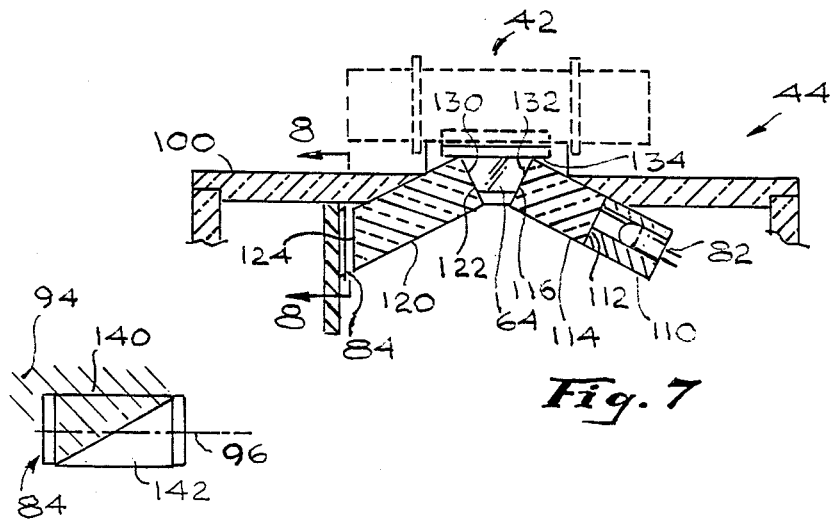
Fig. 7
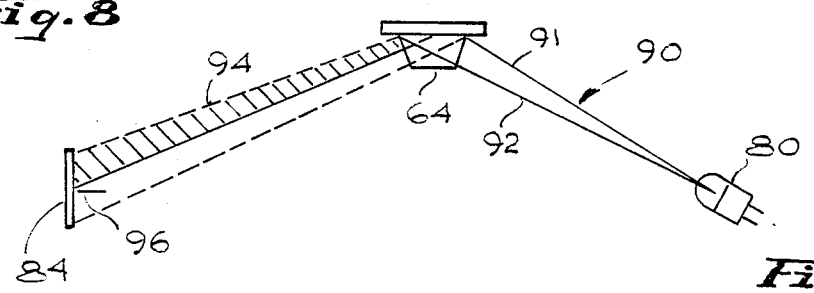
Fig. 8
Fig. 9
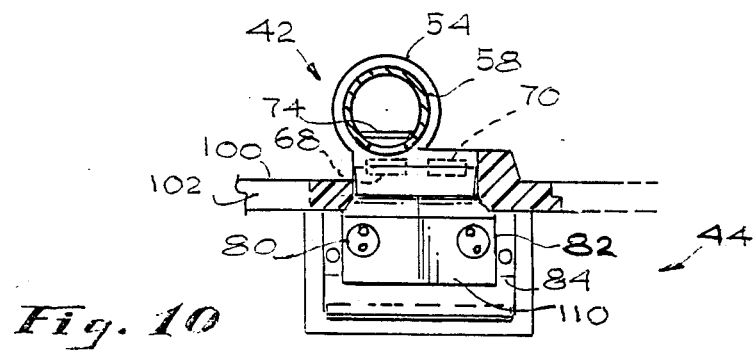
Fig. 10

METHOD AND APPARATUS FOR MEASURING SPECIFIC GRAVITY OF A FLOWING LIQUID

BACKGROUND OF THE INVENTION

This invention relates generally to a system for determining the specific gravity of a liquid and more particularly to a system useful for continually monitoring the specific gravity of a flowing liquid, e.g. urine, discharged from a catheterized patient.

It is well known that the specific gravity of urine constitutes a significant indicator of kidney function and it is accordingly a common hospital practice to periodically check the specific gravity of a patient's urine output. This is typically done by a nurse placing a urine sample on the measurement surface of a clinical refractometer and then sighting, through an eyepiece, the position of a light/dark boundary line projected onto a graduated scale. Such clinical refractometers are well known and readily commercially available; e.g. (1) American Optical Corporation TS Meter and (2) Schuco Model 5711-2020. Alternatively, the specific gravity of a liquid can be automatically measured by pouring a quantity into a Biovation refractometer of the type disclosed in U.S. Pat. No. 4,381,895.

Apparatus is also well known for continually measuring the amount of urine discharged by a catheterized patient and for displaying urine discharge volume and flow rate via a digital electronic display. As an example, one such apparatus comprises the Vitalmetrics, Inc. Model 210 Urine Monitoring System. Related apparatus is disclosed in U.S. Pat. No. 4,448,207 issued May 15, 1984 and U.S. Pat. No. 4,658,834 issued Apr. 21, 1987. Such apparatus is characterized by a disposable container used to collect discharged urine and a microprocessor based measuring means bacteriologically isolated from the urine.

SUMMARY OF THE INVENTION

The present invention is directed to a method and apparatus for continually determining the specific gravity of a flowing liquid.

More particularly, the present invention is directed to a method and apparatus suitable for continually measuring the specific gravity of urine discharged from a catheterized patient.

In accordance with a significant aspect of the invention, specific gravity measuring means are provided which are bacteriologically isolated from the urine. In a preferred embodiment of the invention, an inexpensive and disposable sample container is provided which is mounted in the urine discharge line. The sample container includes a flat measurement surface and defines a flow path so that the flowing urine continually wets the measurement surface. The sample container comprises a disposable item removably mounted adjacent to a permanent detector unit. The detector unit is bacteriologically isolated from the urine and is able, by refractometric measurement, to measure the specific gravity of the urine on the measurement surface.

More specifically, in accordance with the invention the detector unit includes a photovoltaic surface which supplies an electrical output signal indicative of the position of a light/dark boundary line projected thereon. The output signal is preferably used to drive an electronic digital display to provide a readout of the measured specific gravity.

In accordance with the invention, the photovoltaic surface is illuminated by a controlled light source whose rays are reflected off (or refracted through) the measuring surface dependent on their angle of incidence and the specific gravity of the liquid sample. In the preferred embodiment of the invention, the light source output is electronically chopped and the electrical output signal supplied during the on and off phases is compared to eliminate the influence of ambient light.

In accordance with a feature of the preferred embodiment, the photovoltaic surface comprises a rectangular field formed by first and second cells having right triangular surfaces. The hypotenuses of the cells are oriented adjacent to one another so that they extend at an angle to the direction of movement of the light/dark boundary line. In order to determine the position of the boundary line on the surface, the detector electronics, which preferably includes a microcomputer, compares the output of the first and second cells.

In accordance with a still further feature of the preferred embodiment, in order to facilitate calibration and enhance measurement accuracy, a second measurement surface is wetted with a reference liquid, e.g. water. The detector electronic control circuit alternately defines a reference measurement mode during which the reference liquid is illuminated and a sample measurement mode during which the unknown sample is illuminated. The readings derived from the photovoltaic surface during these two modes are then compared and the specific gravity of the sample is determined, as by a table look up operation performed by the microcomputer.

The present invention is embodied in a proposed Vitalmetrics, Inc. Model 240 monitor which received FDA approval to market on May 1, 1984.

BRIEF DESCRIPTION OF THE DRAWING

FIG. 6 is a schematic illustration depicting the principals of refractometry utilized in the preferred embodiment;

FIG. 7 is a sectional view through the detector housing taken substantially along the plane 7—7 of FIG. 3;

FIG. 8 is a sectional view taken substantially along the plane 8—8 of FIG. 7 depicting the split photovoltaic target surface;

FIG. 9 is a schematic illustration further depicting the refractometric principals utilized in accordance with the invention;

FIG. 10 is a sectional view taken substantially along the plane 10—10 of FIG. 3;

DETAILED DESCRIPTION OF EXEMPLARY EMBODIMENT

Figure 1:
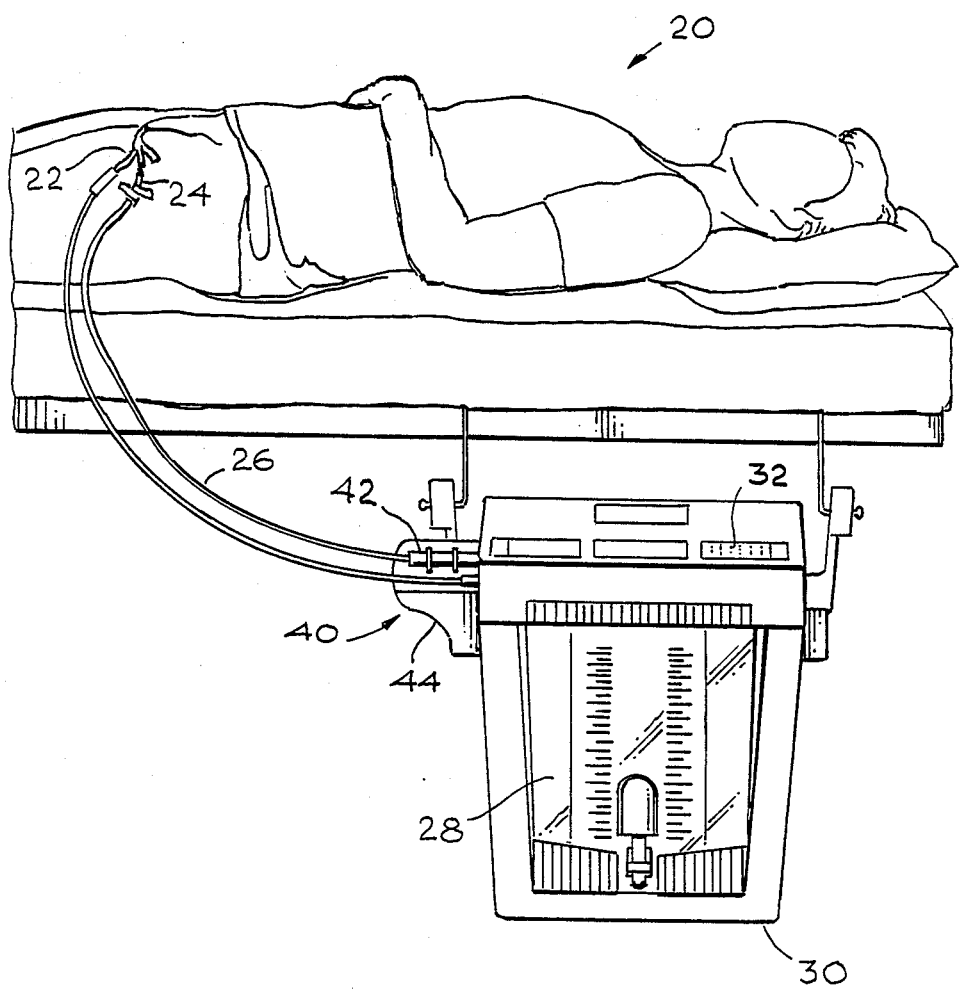
FIG. 1 is a schematic illustration showing a significant application of the invention for monitoring the specific gravity of urine discharged by a catheterized patient into a system for monitoring urine volume and flow rate.

The present invention is directed to a method and apparatus capable of continually measuring the specific gravity of a flowing liquid and providing a visual readout of the measured specific gravity. Although embodiments of the invention are believed to have a wide variety of applications, the invention will be disclosed herein primarily with respect to a significant medical application. More particularly, the invention will be disclosed as an embodiment for continually measuring the specific gravity of urine discharged from a catheterized patient. It is a common hospital procedure to periodically check the specific gravity of a patient's urine because of its significance as an indicator of kidney function Whereas prior art techniques have generally required that a nurse obtain a urine sample and then place it in a clinical refractometer for visual reading or funnel it into a refractometer device for automatic readout, the present invention provides for continually measuring the specific gravity of the urine as it is discharged from the patient into a collection container. Thus, FIG. 1 schematically illustrates a patient 20 having a catheter 22 in place for draining urine from a sample port 24 through a flexible discharge tube 26. The tube 26 extends to a urine collection container 28. The catheter 22, tube 26 and collection container 28 are intended to be disposable items. As is described in the aforementioned Patents in use the urine container 28 is accommodated in a reusable housing 30. The housing includes a measuring means, e.g. ultrasonic, for measuring the volume of liquid in the container 28 and for providing a digital readout of the measured volume and flow rate on a visual display 32.

The apparatus in accordance with the present invention is depicted at 40 in FIG. 1 and functions to measure the specific gravity of urine passing through the discharge tube 26 to the collection container 28. As will be seen hereinafter, the specific gravity measuring apparatus 40 includes a disposable sample container 42 and a cooperating detector 44 which develops information signals for driving the display 32 to visually indicate specific gravity.

Figure 2:
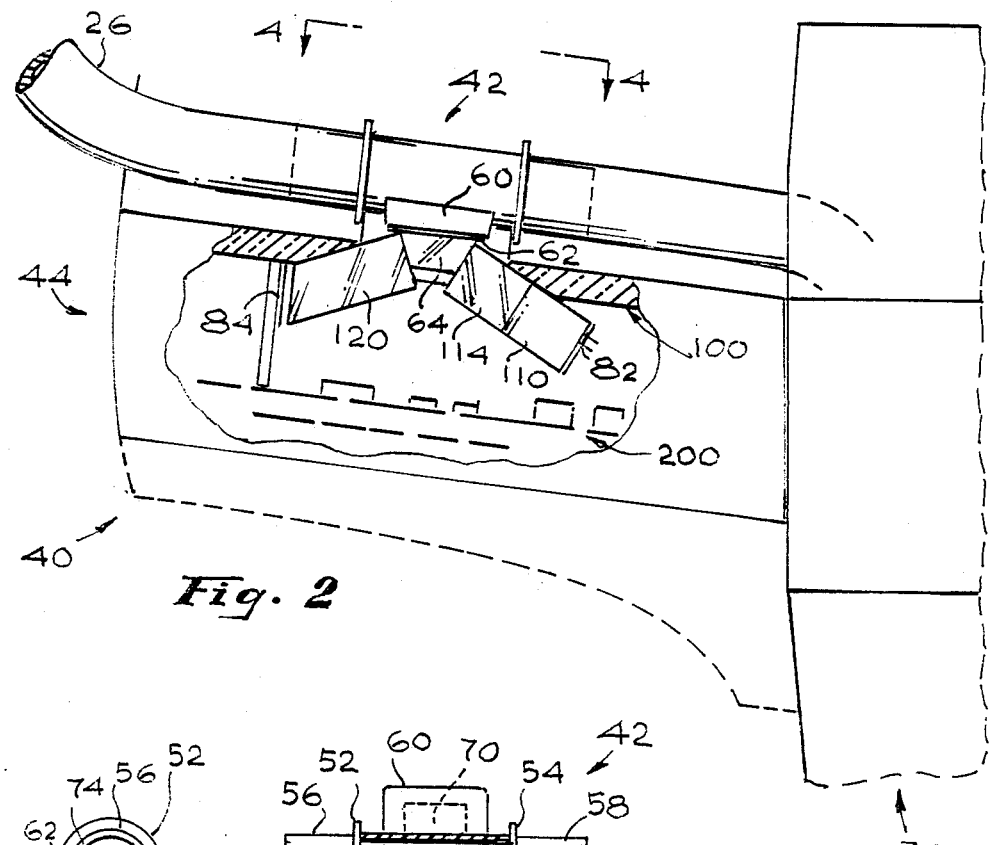
FIG. 2 is a side view, partially broken away, illustrating a preferred embodiment of the invention utilized in conjunction with a prior urine monitoring system.
Figures 4, 5:
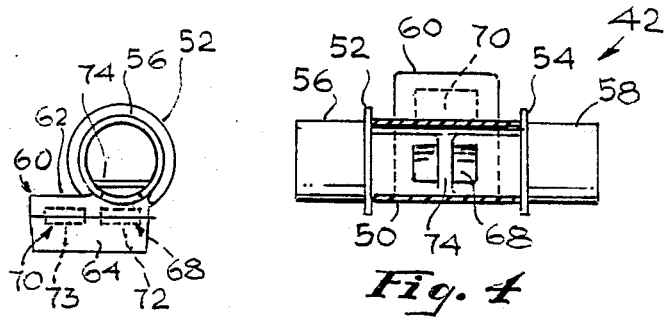
FIG. 4 is a sectional view taken substantially along the plane 4—4 of FIG. 2 and shows the internal construction of the sample container utilized in the preferred embodiment.
FIG. 5 is an end view of the sample container depicted in FIG. 4.

Attention is now directed to FIGS. 2-10 which depict a preferred structural embodiment of a specific gravity measuring apparatus 40 in accordance with the present invention. As is shown in FIG. 2, the disposable sample container 42 is intended to be connected in the discharge tube line 26 so that discharged urine flows therethrough in a manner to be described hereinafter. In use, the sample container 42 precisely mounted and clamped immediately adjacent the detector unit 44 in a manner to be more precisely described hereinafter.

The sample container 42 is preferably formed of plastic material and comprises a substantially tubular structure defined by cylindrical wall 50. External flanges 52 and 54 are spaced along the wall 50 and define end sections 56 and 58. The end sections 56 and 58 are intended to be snugly accommodated in free ends of the flexible discharge tubing 26 to thereby mount the sample container 42 in line to enable the discharged urine to flow therethrough.

The sample container 42 is provided with a shelf member 60 which extends substantially tangentially to the cylindrical wall 50. The shelf member 60 is comprised of a flat upper portion 62 which can be formed integral with the cylindrical wall 50 and a lower prism portion 64 having a truncated triangular cross-section, as depicted in FIGS. 2 and 7. The shelf portions 62 and 64 together define first and second shallow basins 68 and 70. The basins 68 and 70 have substantially flat floor surfaces 72 and 73 which are aligned in the same plane and which define the measurement or interface surfaces for refractometric measurement as hereinafter described.

The basin 68 opens into the internal passageway defined by cylindrical wall 50. Thus, as liquid flows from the discharge tube 26 through the sample container 42, it will continually wash across floor surface 72 of basin 68. Strut 74 overlays the basin 68 and guides the liquid sample onto measurement surface 72.

Basin 70 is closed by flat shelf portion 62 and is used to encapsulate a reference liquid of known specific gravity, preferably distilled water.

The shelf portion 64 is formed of transparent material, preferably plastic, to permit refractometric analysis of the sample liquid in basin 68 and the reference liquid in basin 70. Refractometric techniques for determining the specific gravity of a liquid are well known and will only be briefly discussed herein, initially in connection with schematic diagrams shown in FIGS. 6 and 9. Refractometric measurement to determine specific gravity relies upon the predictable correlation between the index of refraction of a liquid and its specific gravity. The index of refraction can be determined by establishing a condition where a critical angle of light is created and measured. This measurement is directly correlatable to the index of refraction and thus to the specific gravity of the liquid.

The condition necessary to establish a critical angle involves placing the liquid sample against a light transmissive surface (such as glass or plastic) having a known index of refraction. When light rays of various angles strike the mating surface between the liquid sample and the light transmissive solid material, each light ray will either be refracted into the sample or reflected back off the mating surface depending on the angle of each ray. The exact angle at which refraction and reflection are adjacent is called the Critical Angle (CA) and is defined by the equation:

$$CA = \arcsin(N_u/N_s)$$

where $N_u$ is the index of refraction of the liquid sample and $N_s$ is the index of refraction of the solid light transmissive material The light pattern reflected from the mating surface defines a light/dark boundary line which is associated with the ray at the critical angle. This boundary line is projected against a graduated scale in prior commercially available clinical refractometers to permit a nurse to sight the line on the scale and thus determine the specific gravity of a sample.

In accordance with the present invention as depicted in FIG. 6, first and second light sources 80 and 82 are respectively mounted to project light through the prism portion 64 to the measuring surfaces 72, 73 in basins 68, 70. The reflected light pattern formed as a consequence of the incident light on the liquid/solid mating surface is projected onto a photovoltaic sensor 84 to develop an electric signal representing the position of the aforementioned light/dark boundary line and thus the critical angle. FIG. 9 depicts the group of light rays 90 projected by the light source 80. The geometry of the detector should be selected so that the rays 90 include rays greater than and less than the anticipated critical angle for the rage of samples to be measured. Rays at shallower angles 91 will be refracted and pass through the liquid sample. Rays at larger angles 92 will be reflected off the measuring surface, i.e. surface 72, between the liquid sample and solid light transmissive material to cast reflected light 94 on the photovoltaic target 84. This reflected light pattern will show up as a clear light/dark boundary line 96. The boundary line 96 is depicted as a horizontal line in FIG. 8 and it will move perpendicular to its length to a position determined by the specific gravity of the sample being measured. Thus, by determining the position of the line 96 on the photovoltaic target 84, the specific gravity of the sample can be determined.

Figure 3:
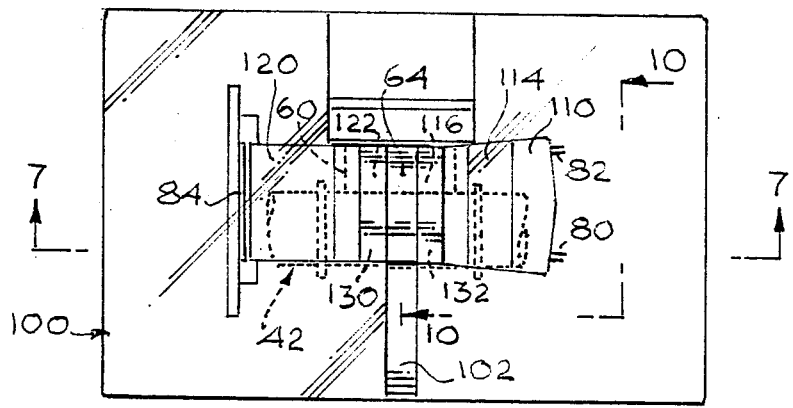
FIG. 3 is a plan view of the detector housing of the preferred embodiment of the invention.

With the foregoing generalized explanation of refractometric measurement, attention is specifically directed to FIGS. 3, 7, and 10 which best illustrate the structural features of the preferred detector apparatus 44. The detector apparatus 44 includes a housing 100 having a channel 102 formed in the upper housing surface. First and second light sources 80, 82, preferably light emitting diodes, are mounted in the housing 100 to one side of the channel 102. Each light source is held within a precisely mounted collar 110 which abuts against a flat rear face 112 of a light transmissive block 114. The front face 116 of block 114 is flat and parallel to the rear face 112.

A photovoltaic target 84 is mounted within the housing 100 on the side of channel 102 opposite to the light sources 80 and 82. A light transmissive block 120 is mounted between the photovoltaic surface 84 and the channel 102. The block 120 has a flat front face 122 adjacent to the channel 102 and a rear face 124 proximate to the photovoltaic target 84.

The front face 116 of light transmissive block 114 and the front face 122 of block 120 are mounted in the housing 100 so as to define a precisely dimensioned cavity therebetween. The aforementioned lower shelf member prism portion 64 is intended to be accommodated in the cavity between the block front faces 116 and 122 so that the opposite side faces 130, 132 thereof extend essentially parallel to the block faces 122 and 116, respectively. The upper edges of the blocks 114 and 120 engage the underside of a ledge 134 on the member 64 to support the member 64 in precise position between the light sources 80, 82 and photovoltaic target 84. With the geometry depicted in FIG. 7, the light emitted by light sources 80, 82 will pass essentially perpendicularly through the interfaces between the collar 110 and block 114 and the block 114 and prism member 64 without refracting. By eliminating these sources of potential distortion, the movement of the boundary line 96 will be solely attributable to the refraction/reflection characteristic created by the interface between the liquid sample and prism member 64.

As will be discussed hereinafter in connection with the description of the control system of FIG. 11, the photovoltaic target 84 is preferably formed of separate first and second photovoltaic cells 140, 142 having right triangle active surfaces. The utilization of separate first and second cells 140, 142 facilitates the resolving of the position of the boundary line 96.

Figure 11:
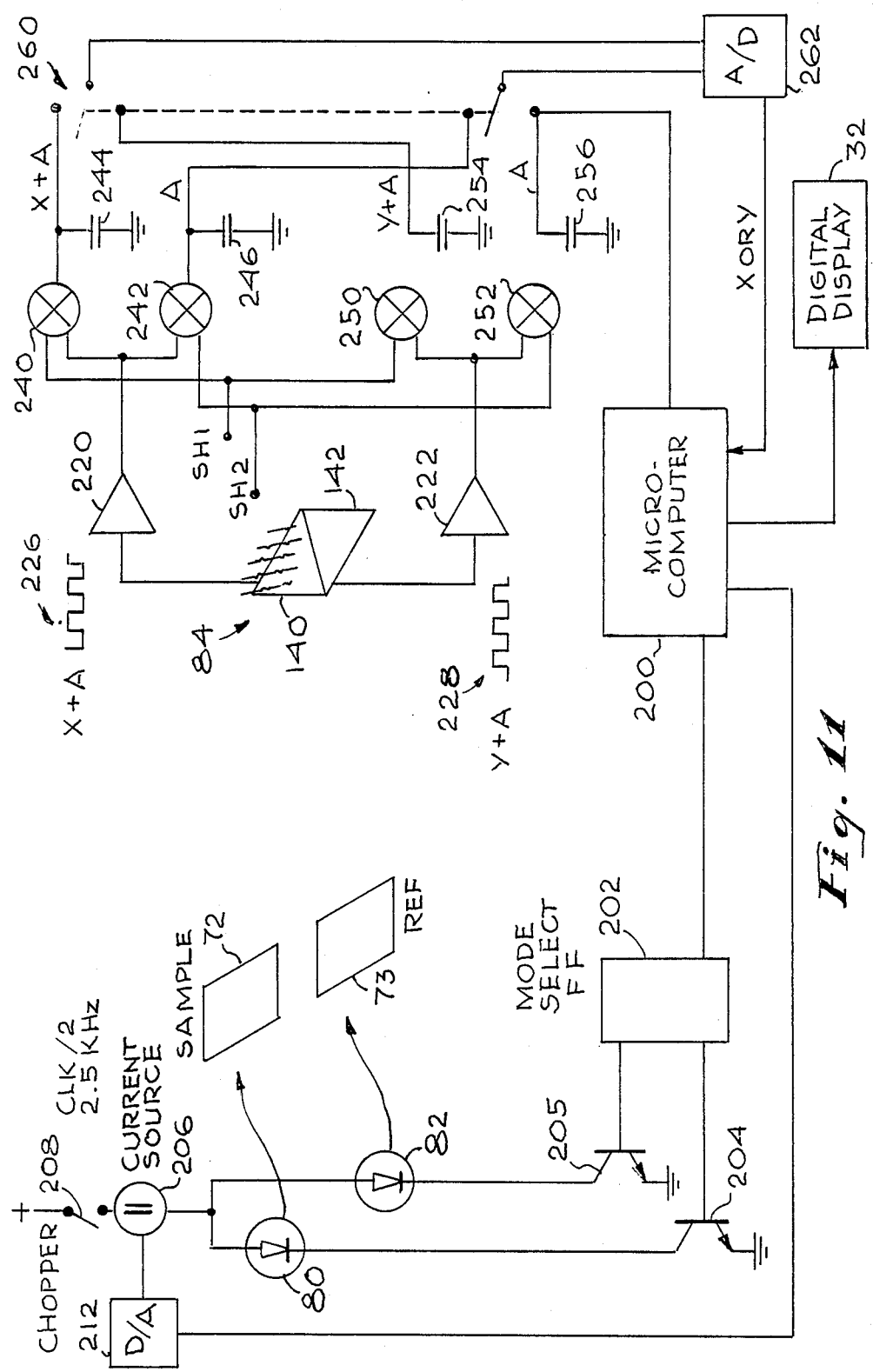
FIG. 11 is a block diagram depicting a preferred microcomputer based detector control system.

Attention is now directed to FIG. 11 which illustrates a preferred detector control system embodiment for the specific gravity measuring apparatus thus far described. To facilitate understanding, FIG. 11 schematically depicts the measurement surface 72 of the liquid sample basin 68 and the interface surface 73 of the reference basin 70. FIG. 11 also depicts the first light source 80 for illuminating the sample measurement surface 72 and the second light source 82 for illuminating the reference measurement surface 73. As will be seen hereinafter, the light sources 80, 82 are energized in a mutually exclusive manner so that during a sample measurement mode the light source 80 will be energized and during a reference measurement mode the light source 82 will be energized. The aforementioned photovoltaic target 84 is used in both the sample measurement mode and reference measurement mode to sense the reflected boundary line. As previously mentioned in connection with FIG. 8, the photovoltaic target 84 is comprised of separate photovoltaic cells 140, 142 which may hereinafter be respectively referred to as the X and Y cells.

The detector control circuit of FIG. 11 includes a microcomputer 200 which controls various operations which are described in greater detail in connection with FIG. 13. Briefly, the microcomputer 200 controls the state of a selector flip-flop 202 which, on a mutually exclusive basis defines the sample measurement mod and the reference measurement mode. During the sample measurement mode, flip-flop 202 enables transistor 204 to permit current flow through light emitting diode 80. A current source 206 is connected to supply current to either light source 80 or 82. An electronic chopper switch 208 is connected to the current source 206 so that during the sample measurement mode, light source 80 is pulsed on and off at a selected frequency, e.g. 2.5 KHz. Similarly, during the reference measurement mode, light source 82 is pulsed at 2.5 KHz. The magnitude of the current supplied by source 206 is controlled by the output of digital to analog converter (DAC) 212 to assure that the light sources 80, 82 emit with appropriate intensity. The DAC 212 is controlled by the microcomputer 200 as will be described in connection with FIG. 13.

The photovoltaic cells 140 and 142 provide electrical output signals to amplifiers 220, 222 respectively. The reason for using a photovoltaic field defined by two right triangle cells 140 and 142 is to better resolve the position of the boundary line 96. Because the light sources 80 and 82 are pulsed, cells 140, 142 will provide substantially square wave outputs 226, 228 to the amplifiers 220, 222. The outputs 226, 228 provided by cells 140, 142 are influenced not only by the light reflected from the sample and reference measurements surfaces, respectively, but also by ambient light. Thus, output 226 is represented in FIG. 11 by X+A where X represents the reflected light falling on cell 140 and A represents an ambient light component. Similarly, output 228 is represented by Y+A.

In order to eliminate the influence of ambient light, the output of amplifier 220 is alternately passed through analog switches 240, 242 operated in synchronism with the chopper switch 208. The analog switches 240, 242 respectively supply sample and hold capacitors 244, 246. The output of amplifier 222 is similarly passed through analog switches 250, 252 to sample and hold capacitors 254, 256.

The microcomputer 200 controls analog switching circuit 260 to concurrently apply either the voltages from capacitors 244 and 246 or the voltages from capacitors 254 and 256 to the analog to digital converter (ADC) 262. An input differential amplifier (not shown) is associated with the converter 262 to eliminate the influence of the ambient light from the signals output by amplifiers 220, 222. That is, as should be appreciated, capacitor 244 stores a voltage representative of X+A, attributable to light reflected onto cell 140 during the on time of either light source 80 or 82 plus an ambient light component. On the other hand capacitor 246 stores a voltage representative of the ambient light falling on cell 140 during the off state of light sources 80, 82. The differential amplifier associated with converter 262 subtracts the ambient light component A from the voltage stored by capacitor 244 to thereby output a digital representation X which is indicative of the light reflected onto the cell 140 during the on state of light sources 80, 82. The output of the converter 262 is supplied to the microcomputer 200 which, by a table lookup operation, determines the specific gravity of the sample and drives the aforementioned digital display 32.

Figure 12:
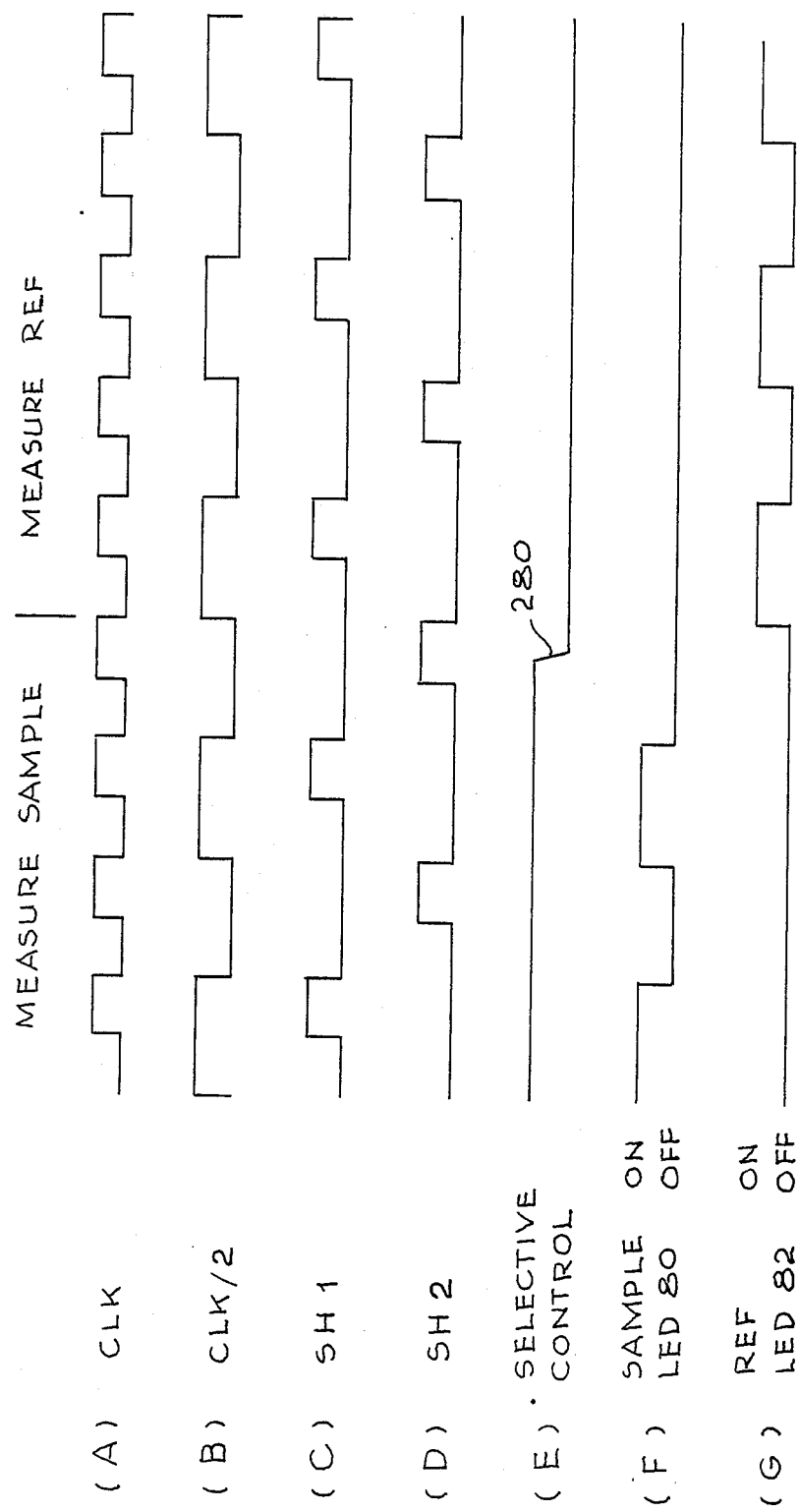
FIG. 12 is a timing chart depicting wave forms occurring in the control system of FIG. 11.

In order to better understand the operation of the control circuit of FIG. 11, attention is directed to FIG. 12 which comprises a timing chart. Line A represents a clock signal which has been assumed to be 5.0 KHz. Line B represents the clock signal divided by 2. Lines C and D respectively show timing signals SH1 and SH2 for respectively enabling the analog switches 240, 250 and 242, 252. These control signals SH1 and SH2, as previously noted, must be synchronized to the on/off states of the light sources 80, 82.

Line E of FIG. 12 depicts the selector control signal supplied by microcomputer 200 to the flip-flop 202. Transition 280 on line E represents a microcomputer command to switch from the sample measurement mode to the reference measurement mode. Lines F and G respectively represent the chopping of the light sources 80, 82 during the sample measurement and reference measurement modes respectively.

Figure 13:
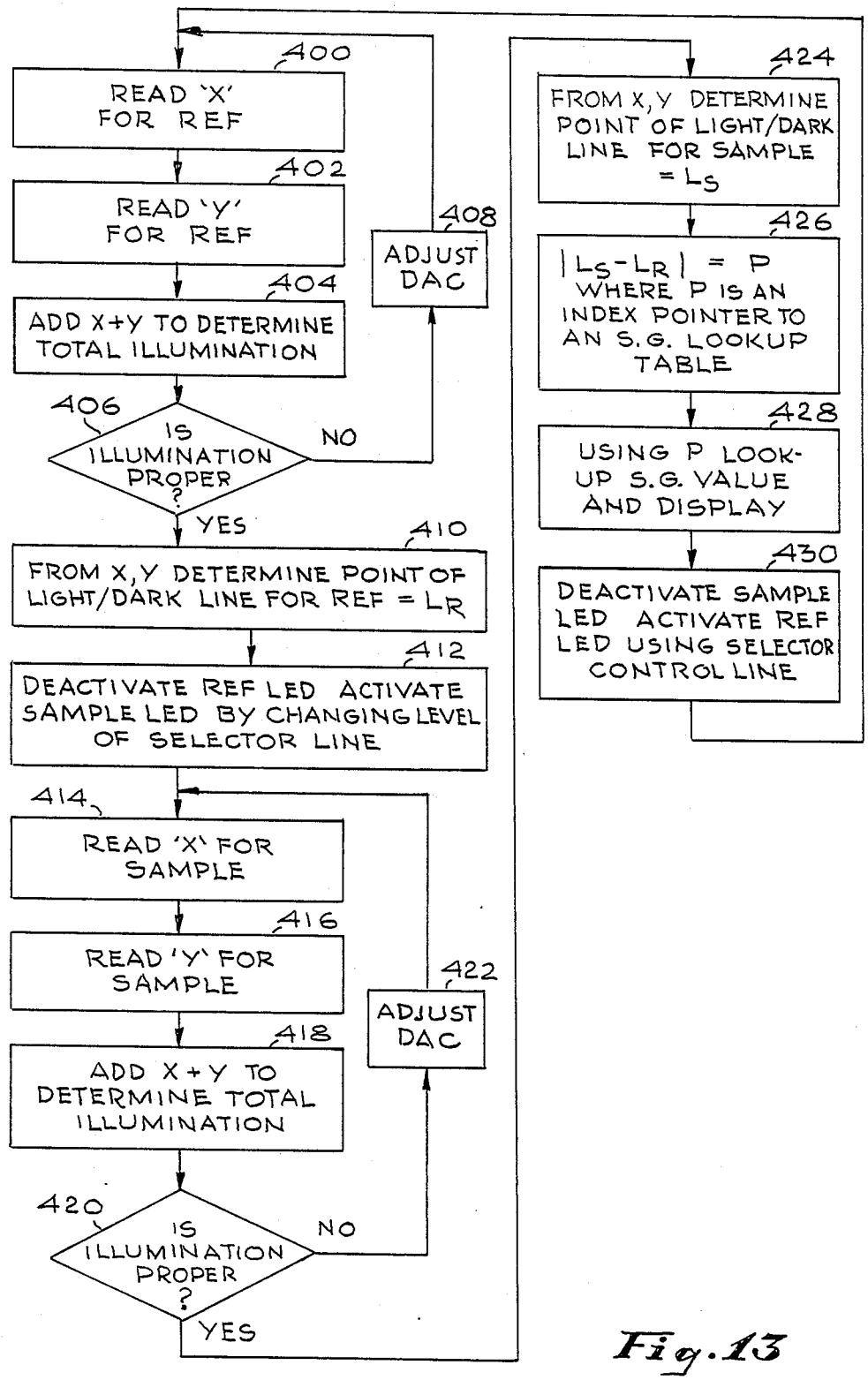
FIG. 13 is a flow chart depicting the operation of the microcomputer of FIG. 11.

Attention is now directed to FIG. 13 which comprises a flow chart defining the operation of the microcomputer 200 and the overall operation of the detector control circuit of FIG. 11. From what has been said thus far, it should be appreciated that the microcomputer alternately defines the sample measurement and reference measurement modes. FIG. 13 arbitrarily starts with block 400 during the reference measurement mode and depicts the microcomputer reading the value X from the converter 262. It will be recalled that the value X represents the light intensity reflected onto cell 140 with the influence of ambient light eliminated.

Thereafter, the value Y is read, as depicted in block 402. The microcomputer then adds the read values X and Y in block 404 to determine the total illumination reflected onto cells 140 and 142. Decision block 406 then tests to see whether the total illumination is proper. If not, the microcomputer adjusts the DAC 212 in block 408 and returns to block 400. If decision block 406 indicates that the illumination level is proper, then the microcomputer 200 progresses to block 410 to determine the position $L_R$ of the boundary line 96 during the reference measurement mode. This value $L_R$ is stored by the microcomputer.

Thereafter, in block 412, the reference LED 82 is deactivated and the sample LED 80 is activated. The X and Y values for the sample are then read in blocks 414 and 416. Block 418 sums the read X and Y values to determine total illumination and block 420 then tests to see whether illumination is proper. If not, then the DAC 212 is adjusted as represented by block 422. If illumination is proper, then the position of the boundary line 96 for the sample, i.e. $L_S$ is determined, as represented by block 424.

Block 426 thereafter determines a value P based on the difference between the values $L_S$ and $L_R$. That is, inasmuch as the specific gravity of the liquid reference is known, it is preferable to determine the deviation of the boundary line position caused by the sample, rather than the absolute position of the boundary line. This deviation in boundary line position caused by the sample, is represented by P in FIG. 13 and is used by the microcomputer as an index pointer for a table lookup operation to retrieve the specific gravity value for the sample. This operation is represented by block 428 which also indicates that this specific gravity value derived from the table lookup operation is used to drive the digital display 32. After the execution of block 428, block 430 is executed to switch from the sample measurement mode to the reference measurement mode.

From the foregoing, it should now be appreciated that a method and apparatus have been disclosed herein for continually measuring the specific gravity of a flowing liquid. Although an embodiment of the invention is particularly useful in a medical apparatus for monitoring urine discharge, the invention is also applicable to other medical and industrial applications for determining the specific gravity of a flowing liquid on a continuous basis. Accordingly, although a preferred embodiment of the invention has been disclosed herein, it is recognized that modifications and variations will occur to those skilled in the art which fall within the intended scope of the appended claims. Thus, it is intended that the claims be interpreted to cover all equivalent modifications and variations.

We claim:

1. Medical apparatus for automatically continually measuring the specific gravity of liquid discharged from a catheter coupled to a patient, said apparatus comprising:

a collection container;

tubing means including a tubular section having an internal passageway for carrying liquid discharged from said catheter through said internal passageway to said container;

said tubular section being defined by a tubular wall including a light transparent shelf member having a flat internal surface located in said internal passageway and a flat external surface located external to said internal passageway whereby said discharged liquid can flow across said internal surface;

a prism formed of light transparent material having a flat base face and first and second flat side faces;

said prism being attached to said tubular section externally of and biologically isolated from said internal passageway with said base face substantially contiguous with said external surface;

detector means including spaced first and second flat surfaces defining an open cavity therebetween, said cavity being shaped and dimensioned to removably receive said prism with said prism first and second side faces respectively contiguous with said detector means first and second flat surfaces, and with said detector means being biologically isolated from said internal passageway;

said detector means including light source means for illuminating, through said prism and shelf member, a liquid sample on said internal surface at angles of incidence greater and less than a critical angle related to the specific gravity of the liquid sample;

said detector means further including photosensor means responsive to light reflected from said liquid sample, through said shelf member and said prism, for producing an output signal indicative of ther critical angle and specific gravity of said liquid sample, said photosensor means comprising first and second cells, each cell defining a right triangle active surface, oriented with the hypotenuse of each cell adjacent to the hypotenuse of the other cell to thereby form a substantially rectangular active field;

said photosensor means being oriented such that light reflected from said liquid sample defines a ligth-/dark boundary line on said rectangular active field extending parallel to one side thereof wherein said photosensor means output signal is a function of the position of said boundary line on said field and indicative of the critical angle and specific gravity of said liquid sample.

2. The apparatus of claim 1 including means for controlling said light source means to alternately define on and off states of illumination; and means for comparing said photosensor means output signal during said on and off states to eliminate the influence of ambient light.

3. The apparatus of claim 2 wherein each of said first and second cells produces an output signal component related to the amount of light incident on the active surface thereof; and wherein said photosensor means includes means responsive to said first and second cell output signal components for producing said output signal.

4. The apparatus of claim 1 wherein each of said first and second cells produces an output signal component related to the amount of light incident on the active surface thereof;

means for alternately switching said light source means illumination on and off;

means for comparing said first cell output signal component during said on and off states to produce a first cell net output signal component substantially independent of ambient light level;

means for comparing said second cell output signal component during said on and off states to produce a second cell net output signal component substantially independent of ambient light level; and wherein said photosensor means includes means responsive to said first and second cell net output signal components for producing said output signal.

5. The apparatus of claim 1 including means responsive to said photosensor means output signal for digitally displaying the specific gravity of said liquid sample.

6. The apparatus of claim 1 wherein said shelf member defines a shallow basin open to said internal passageway and wherein said internal surface is located in said basin; and guide means mounted adjacent to said basin for guiding said discharged liquid across said internal surface.

7. The apparatus of claim 1 wherein said shelf member includes a second flat internal surface;

a reference liquid of known specific gravity encapsulated on said second surface;

means for periodically causing said light source means to illuminate, through said prism and shelf member, said reference liquid at angles of incidence greater and less than the critical angle of said reference liquid; and wherein said photosensor means includes means for producing a reference output signal concurrent with the illumination of said reference liquid, indicative of the critical angle of said reference liquid; and means for comparing said photosensor means output signal with said reference output signal and for outputting a signal which is a function of said comparison.

* * * * *